United States Patent
Bom

(10) Patent No.: US 8,309,598 B2
(45) Date of Patent: Nov. 13, 2012

(54) COOLING COMPOUNDS

(75) Inventor: David C. Bom, Cincinnati, OH (US)

(73) Assignee: Givaudan S.A., Vernier (CH)

( * ) Notice: Subject to any disclaimer, the term of this patent is extended or adjusted under 35 U.S.C. 154(b) by 789 days.

(21) Appl. No.: 12/339,184

(22) Filed: Dec. 19, 2008

(65) Prior Publication Data
US 2009/0163572 A1 Jun. 25, 2009

Related U.S. Application Data

(60) Provisional application No. 61/008,178, filed on Dec. 19, 2007.

(51) Int. Cl.
- A61K 31/39 (2006.01)
- A61K 31/385 (2006.01)
- C07D 327/06 (2006.01)
- C07D 339/08 (2006.01)

(52) U.S. Cl. .......................... 514/434; 549/15
(58) Field of Classification Search .............. 514/434; 549/15
See application file for complete search history.

(56) References Cited

U.S. PATENT DOCUMENTS

| | | | |
|---|---|---|---|
| 4,150,052 | A | 4/1979 | Watson et al. |
| 4,285,984 | A | 8/1981 | Huber |
| 7,414,152 | B2 | 8/2008 | Galopin et al. |
| 2003/0072842 | A1 | 4/2003 | Johnson et al. |
| 2006/0035008 | A1 | 2/2006 | Virgallito et al. |
| 2006/0142177 | A1 | 6/2006 | Furrer et al. |
| 2006/0276667 | A1 | 12/2006 | Galopin et al. |
| 2008/0176945 | A1 | 7/2008 | Galopin et al. |
| 2008/0253974 | A1 | 10/2008 | Galopin et al. |
| 2008/0305051 | A1 | 12/2008 | Cole et al. |
| 2008/0311232 | A1 | 12/2008 | Furrer et al. |
| 2008/0319055 | A1 | 12/2008 | Cole et al. |

FOREIGN PATENT DOCUMENTS

| | | |
|---|---|---|
| WO | WO 97/15308 A1 | 5/1997 |
| WO | WO 2005/049553 A1 | 6/2005 |
| WO | WO 2007/019719 A1 | 2/2007 |

OTHER PUBLICATIONS

Arnoldi, et al., "Progress in isovanillyl sweet compounds", Food Chemistry, 1996, 56, 247-253.
Arnoldi, et al., "Sweet isovanillyl derivatives", J. Agric. Food Chem., 1998, 46, 4002-4010.
Bassoli, et al., "Quantitative structure-activity relationships of sweer isovanillyl derivatives", Quant. Struct.-Act. Relat., 2001, 20, 3-16.
Bassoli, et al., "Enantiodifferentiation in taste perception of isovanillic derivatives", Tetrahedron: Assymetry, 2000, 11, 3177-3186.

*Primary Examiner* — Kristin Bianchi
(74) *Attorney, Agent, or Firm* — Curatolo Sidoti Co., LPA; Joseph G. Curatolo; Salvatore A. Sidoti

(57) ABSTRACT

A method of providing a cooling sensation to the skin or the mucous membranes of the body, comprising the application thereto of at least one compound of the Formula I

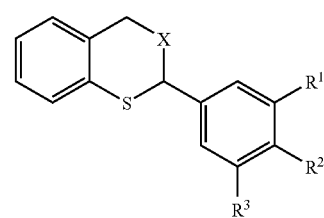

in which X is selected from S and O, $R^1$ is selected from H and OMe, $R^2$ is selected from OH, OMe and OEt, and $R^3$ is selected from H and OH. Some of the compounds provide simultaneously cooling and sweetening effects.

11 Claims, No Drawings

COOLING COMPOUNDS

CROSS REFERENCE TO RELATED APPLICATIONS

This application claims the benefit of the filing date, under 35 U.S.C. §119(e), of U.S. Provisional Patent Application Ser. No. 61/008,178, filed Dec. 19, 2007, which application is incorporated by reference herein.

TECHNICAL FIELD

This invention relates to chemical compounds having a cooling effect.

BACKGROUND

Chemical compounds that have a cooling effect on the skin, mouth and mucous membranes are well known and widely used. Among the most successful of these are various carboxamide derivatives. Typical examples of such materials that have been successfully marketed are those sold under the trade names WS-3 and WS-23. However, despite the considerable commercial success of these materials, there has been continued searching for other compounds with cooling properties and additional advantages.

DESCRIPTION

It has now been found that a class of compounds has cooling properties, and in addition, some members of the class exhibit additional desirable properties. There is therefore provided a method of providing a cooling sensation to the skin, the mouth or the mucous membranes of the body, comprising the application thereto of at least one compound of the Formula I

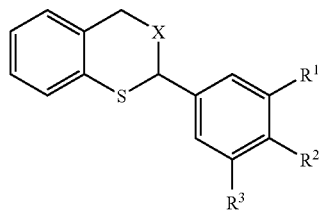

I in which X is selected from S and O, $R^1$ is selected from H and OMe, $R^2$ is selected from OH, OMe and OEt and $R^3$ is selected from H and OH.

By "OMe" is meant methoxy and by "OEt" is meant ethoxy.

The compounds of the formula give rise to R- and S-enantiomers. These may be resolved if desired, but this adds to the expense of the process, often without gaining any advantage, and for the most part the compounds may be used as racemates.

Illustrative cooling compounds are 4-(4H-benzo[d][1,3]oxathiin-2-yl)benzonitrile and 4-(4H-benzo[d][1,3]dithiin-2-yl)benzonitrile.

In a particular embodiment, there can be simultaneously supplied cooling and sweetening. Therefore, there is also provided a method of providing simultaneously to the mouth cooling and sweetening effects, comprising the application to the mouth of a compound comprising at least one of 5-(4H-benzo[d][1,3]oxathiin-2-yl)-2-ethoxyphenol; 5-(4H-benzo[d][1,3]oxathiin-2-yl)-2-methoxyphenol; 4-(4H-benzo[d][1,3]oxathiin-2-yl)phenol; 5-(4H-benzo[d][1,3]dithiin-2-yl)-2-ethoxyphenol; 5-4H-benzo[d][1,3]dithiin-2-yl)-2-methoxyphenol; 4-(4H-benzo[d][1,3]dithiin-2-yl)phenol or mixtures thereof.

Some of the compounds useful in the abovementioned method are novel compounds. There is therefore also provided the following novel compounds:
5-(4H-benzo[d][1,3]oxathiin-2-yl)-2-ethoxyphenol,
4-(4H-benzo[d][1,3]oxathiin-2-yl)phenol,
4-(4H-benzo[d][1,3]oxathiin-2-yl)benzonitrile,
5-(4H-benzo[d][1,3]oxathiin-2-yl)-2,3-dimethoxyphenol,
5-(4H-benzo[d][1,3]dithiin-2-yl)-2-ethoxyphenol,
4-(4H-benzo[d][1,3]dithiin-2-yl)phenol,
4-(4H-benzo[d][1,3]dithiin-2-yl)benzonitrile,
5-(4H-benzo[d][1,3]dithiin-2-yl)-2,3-dimethoxyphenol.

In use, the compounds may be simply blended into an application in a proportion sufficient to provide the desired cooling or cooling/sweetening effect. A suitable level may be determined in every case by simple experimentation, but as a general guide the level is from 0.01 ppm to 100 ppm, particularly from 0.01 ppm to 50 ppm, more particularly from 1 ppm to 100 ppm, and most particularly from 1 ppm to 50 ppm.

By "application" is meant any practical use of the compounds in which cooling or cooling/sweetening is desired. Typical (and non-limiting) applications include all kinds of foodstuffs, beverages, confectionery, medicaments, oral care products such as toothpastes and mouthwashes, and personal care products such as cosmetics, creams and salves.

In the formulation of any such products, all of the normal materials of the art may be used in art-recognised proportions. A non-limiting list includes surfactants and emulsifiers, gelling agents, pigments, dyestuffs and other colouring matters, agents against deterioration and degradation, such as light stabilisers, antimicrobial agents, antifungal agents, fillers and extenders, abrasive materials and liposomes.

The compounds may also be used in conjunction with known cooling and sweetening agents. Non-limiting examples of known cooling agents include menthol, menthone, isopulegol, N-ethyl p-menthanecarboxamide (WS-3), N,2,3-trimethyl-2-isopropyl-butanamide (WS-23), menthyl lactate, menthone glycerine acetal (Frescolat® MGA), mono-menthyl succinate (Physcool®), mono-menthyl glutarate, O-menthyl glycerine (CoolAct® 10) and 2-sec-butyl-cyclohexanone (Freskomenthe®), ethyl 2-(2-isopropyl-5-methylcyclohexane carboxamido)acetate (WS-5) and the menthyl pyrrolidone carboxylic acid compounds sold under the commercial name "Questice". Non-limiting examples of known sweetening agents include cyclamate, nutrasweet (aspartame), sucrose, fructose, sucralose, neohesperidin dihydrochalcone, rebaudioside, stevioside, neotame, mannitol, erithrytol, xylose, rhamnose, Luo Han Guo extract, mogriside (V), stevia extract, and thaumatin.

In addition, the compounds may be combined with the cooling compounds described in International Published Applications WO 2005/049553 and WO 2007/019719, in particular with N-(4-cyanomethylphenyl) p-menthanecarboxamide, particularly (1R,2S,5R)—N-(4-cyanomethylphenyl) p-menthanecarboxamide, and N-(2-pyridin-2-ylethyl) p-menthane-carboxamide, particularly (1R,2S,5R)—N-(2-pyridin-2-ylethyl) p-menthanecarboxamide.

The compounds may be used in all applications in which it is desirable to impart a cooling sensation to the skin or the mucous membranes of the body. Examples of these include:

Consumable products, including, but not limited to all food products, food additives, nutraceuticals, pharmaceuticals and any product placed in the mouth including chewing gum, oral care products, and oral hygiene products including but not limited to, cereal products, rice products, tapioca products, sago products, baker's products, biscuit products, pastry products, bread products, confectionery products, dessert products, gums, chewing gums, mouthwash, dental floss, flavored or flavor-coated straws, flavor or flavor-coated food/beverage containers, chocolates, ices, honey products, treacle products, yeast products, baking-powder, salt and spice products, savory products, mustard products, vinegar products, sauces (condiments), tobacco products, cigars, cigarettes, processed foods, cooked fruits and vegetable products, meat and meat products, jellies, jams, fruit sauces, egg products, milk and dairy products, yoghurts, cheese products, butter and butter substitute products, milk substitute products, soy products, edible oils and fat products, medicaments, beverages, carbonated beverages, alcoholic drinks such as beers, wines and spirits, non-alcoholic drinks such as soft drinks, mineral and aerated waters, fruit drinks, fruit juices, coffee, artificial coffee, tea, cocoa, including forms requiring reconstitution including, without limitation, beverage powder, milk based beverage powder, sugar-free beverage powder, beverage syrup, beverage concentrate, instant coffee, instant tea, instant cocoa, and coffee whitener. Food extracts, plant extracts, meat extracts, condiments, gelatins, pharmaceutical and non-pharmaceutical gums, tablets, lozenges, drops, emulsions, elixirs, syrups and other preparations for making beverages, and combinations thereof.

Oral care products, as hereinabove mentioned, include any composition applied to the oral cavity for the purposes of cleaning, freshening, healing, deodorising the cavity or any part thereof, may include, but are not limited to, toothpastes, tooth gels, tooth powders, tooth whitening products, mouthwashes, lozenges, dental floss, toothpicks, anti-plaque and anti-gingivitis compositions, throat lozenges, throat drops, inflammatory compositions, compositions for treatment of nasal symptoms, cold symptoms and upper gastrointestinal tract distress, compositions for cold relief, for alleviating discomfort of hot flash, and gargle compositions.

Cosmetic products, such as aftershave lotions, baby products, including lotions, oils, powders, creams and shampoos, basecoats and undercoats, bath preparations, including capsules, oils, tablets, salts, soaps and detergents, beard softeners, blushers, body and hand preparations, bubble baths, cleaning products, colognes and toilet waters, cuticle softeners, dentifrices, deodorants, depilatories, douches, eye lotions, eye makeup preparations including eye makeup removers, eye shadows, eyebrow pencils and eyeliners, face and neck preparations, face powders, feminine hygiene deodorants, foot powders and sprays, foundations, fragrance preparations, hair and scalp preparations including bleaches, colour sprays and other colouring preparations such as dyes and colours, hair lighteners with colour, hair conditioners, hair preparations, hair rinses, hair shampoos, hair sprays, hair straighteners, hair tints, hair tonics, hair wave sets, indoor tanning preparations, leg and body paints, lipsticks, makeup bases, makeup preparations including fixatives, manicuring preparations, mascara, men's talcum, moisturising preparations, nail creams and lotions, nail extenders, nail polish and enamel removers, nail polish and enamels, night skin care preparations, paste masks, perfumes, permanent waves, personal cleanliness products, powders, preshave lotions, rouges, sachets, shampoos, shaving cream, shaving preparations miscellaneous, shaving soap, skin care preparations, including fresheners, suntan preparations including gels, creams and liquids.

The method is now further described with reference to the following non-limiting examples. The compounds used are compounds of the Formula I as follows:

| Example No. | X | R$^1$ | R$^2$ | R$^3$ |
|---|---|---|---|---|
| 1 | O | H | OEt | OH |
| 2 | O | OMe | OMe | OH |
| 3 | O | H | CN | H |
| 4 | O | H | OH | H |
| 5 | S | H | OEt | OH |
| 6 | S | OMe | OMe | OH |
| 7 | S | H | OH | H |

Example 1

Preparation of 5-(4H-benzo[d][1,3]oxathiin-2-yl)-2-ethoxyphenol a.) 4-ethoxy-3-hydroxybenzaldehyde was First Prepared as Described by Wymann et. al. (Synthetic Comm., 1988, pp. 1379-1384).

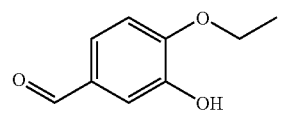

The compound was a light yellow solid. $^1$H NMR (300 MHz, CDCl$_3$, ppm) δ 1.49 (t, J=7 Hz, 3H); 4.21 (q, J=7 Hz, 2H); 5.94 (br s, 1H); 6.95 (d, J=8 Hz, 1H); 7.39-7.45 (m, 2H); 9.83 (s, 1H); $^{13}$C NMR (75 MHz, CDCl$_3$, ppm) δ 14.8; 65.1; 111.0; 114.2; 124.7; 130.6; 146.4; 151.4; 191.3, MS calculated for C9H10O3+H 167 observed 167.

b.) 5-(4H-benzo[d][1,3]oxathiin-2-yl)-2-ethoxyphenol

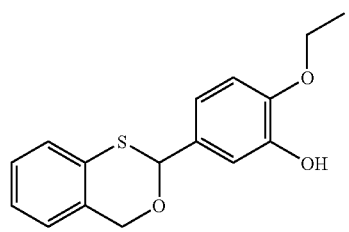

Hydrogen chloride gas was bubbled for three minutes at 22° C. through a solution of the product from step a) (0.99 g, 5.95 mmol) and (2-mercaptophenyl)methanol (1 g, 7.14 mmol) in dichloromethane (25 ml). After an additional 15 min., the reaction mixture was poured into saturated NaHCO$_3$ (50 ml) and extracted with dichloromethane (2×75 ml). The combined organic layer was washed with brine (30 ml), dried (Na$_2$SO$_4$), filtered and concentrated providing a crude solid. This solid was triturated with hexane and then purified by flash chromatography using a gradient of hexanes (100%) up to hexanes (70%:30%). Concentration of the product containing fractions provided the above subtitle compound (0.45 g, 26%) as a cream colored solid. $^1$H NMR (300 MHz, CDCl$_3$, ppm) δ 1.43 (t. J=7 Hz, 3H); 4.10 (q J=7 Hz, 2H); 5.04 (d, J=15 Hz, 1H); 5.10 (d, J=15 Hz, 1H); 5.72 (s, 1H): 6.01 (s, 1H); 6.83 (d, J=8 Hz, 1H); 6.95-7.04 (m, 2H); 7.05-7.18 (m, 4H); $^{13}$C NMR (75 MHz, CDCl$_3$, ppm) δ 15.0; 64.8; 70.5; 82.8; 111.6; 113.1; 118.5; 125.0; 125.9; 127.4; 127.5; 129.9; 131.4; 133.1; 146.0; 146.5; MS calculated for C16H16O3S+H 289 observed 289.

Example 2

Preparation of 5-(4H-benzo[d][1,3]oxathiin-2-yl)-2,3-dimethoxyphenol

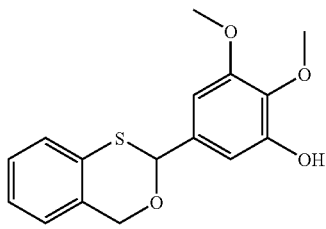

Following the same procedure as outlined in Example 1 step b), 3-hydroxy-4,5-dimethoxybenzaldehyde (1.08 g, 5.95 mmol) and (2-mercaptophenyl)methanol (1 g, 7.14 mmol) in dichloromethane (30 ml) %% ere treated with hydrogen chloride gas. After workup and chromatography, as in example 1 step b), the subtitle compound was obtained (1.06 g, 59%) as a white solid. $^1$H NMR (300 MHz, CDCl$_3$, ppm) δ 3.88 (s, 3H); 3.89 (s, 3H); 5.04-5.14 (m, 2H); 5.85 (s, 1H); 6.01 (s, 1H); 6.72 (d, J=2 Hz, 1H); 6.76 (d, J=2 Hz, 1H); 6.98-7.04 (m, 1H); 7.05-7.19 (m, 3H); $^{13}$C NMR (75 MHz, CDCl$_3$, ppm) δ 56.1; 61.1; 70.5; 82.9; 102.4; 106.7; 125.1; 126.0; 127.48; 127.5; 129.8; 132.9; 134.2; 136.1; 149.4; 152.8; MS calculated for C16H16O4S+H 305 observed 305.

Example 3

Preparation of 4-(4H-benzo[d][1,3]oxathiin-2-yl)benzonitrile

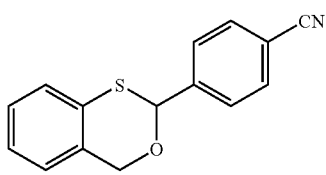

Following the same procedure as outlined in Example 1 step b), 4-formylbenzonitrile (0.78 g, 5.95 mmol) and (2-mercaptophenyl)methanol (1 g, 7.14 mmol) in dichloromethane (30 ml) were treated with hydrogen chloride gas. After workup and chromatography, as in example 1 step b), the subtitle compound was obtained (1.12 g, 75%) as a white solid. $^1$H NMR (300 MHz, CDCl$_3$, ppm) δ 5.10 (s, 2H); 6.15 (s, 1H); 7.04-7.21 (m, 4H); 7.59-7.68 (m, 4H); $^{13}$C NMR (75 MHz, CDCl$_3$, ppm) δ 70.2; 81.7; 112.8; 118.6; 125.6; 126.1; 127.1; 127.6; 127.7; 129.9; 132.0; 132.6; 143.4; MS calculated for C15H11NOS+H 254 observed 254.

Example 4

Preparation of 4-(4H-benzo[d][1,3]oxathiin-2-yl)phenol

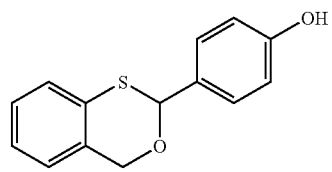

Following the same procedure as outlined in Example 1 step b), 4-hydroxybenzaldehyde (0.73 g, 5.95 mmol) and (2-mercaptophenyl)methanol (1 g, 7.14 mmol) in dichloromethane (30 ml) were treated with hydrogen chloride gas. After workup and chromatography, as in example 1 step b), the subtitle compound was obtained (0.91 g, 63%) as a white solid. $^1$H NMR (300 MHz, CDCl$_3$, ppm) δ 5.04 (d, J=15 Hz, 1H); 5.10 (d, J=15 Hz, 1H); 5.19 (s, 1H); 6.02 (s, 1H); 6.76-6.81 (m, 2H); 6.96-7.03 (m, 1H); 7.04-7.19 (m, 3H); 7.35-7.42 (m, 2H); $^{13}$C NMR (75 MHz, CDCl$_3$, ppm) δ 70.6; 82.8; 115.7; 125.1; 126.0; 127.5; 128.4; 129.9; 130.6; 133.1; 156.4; MS calculated for C14H12O2S+H 245 observed 245.

Example 5

Preparation of 5-(4H-benzo[d][1,3]dithiin-2-yl)-2-ethoxyphenol a.) 4-ethoxy-3-hydroxybenzaldehyde was First Prepared as Described by Wymann et. al. (Synthetic Comm., 1988, pp. 1379-1384).

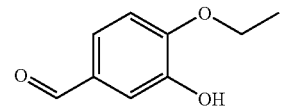

The compound was a light yellow solid. $^1$H NMR (300 MHz, CDCl$_3$, ppm) δ 1.49 (t, J=7 Hz, 3H); 4.21 (q, J=7 Hz, 2H); 5.94 (br s, 1H); 6.95 (d, J=8 Hz, 1H): 7.39-7.45 (m, 2H); 9.83 (s, 1H); $^{13}$C NMR (75 MHz, CDCl$_3$, ppm) δ 14.8; 65.1; 111.0; 114.2; 124.7; 130.6; 146.4; 151.4; 191.3; MS calculated for C9H10O3+H 167 observed 167.

b.) 5-(4H-benzo[d][1,3]dithiin-2-yl)-2-ethoxyphenol

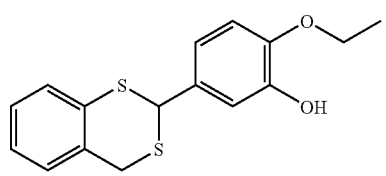

Hydrogen chloride gas was bubbled for three minutes at 22° C. through a solution of 4-ethoxy-3-hydroxybenzaldehyde (0.50 g, 3.0 mmol) and 2-(mercaptomethyl)benzenethiol (0.52 g, 3.3 mmol) in dichloromethane (15 ml). After an additional 15 min. the reaction mixture was poured into saturated NaHCO$_3$ (50 ml) and extracted with dichloromethane (2×75 ml). The combined organic layer was washed with brine (30 ml), dried (Na$_2$SO$_4$), filtered and concentrated providing a crude solid. This solid was triturated with hexane and then purified by flash chromatography using a gradient of hexanes (100%) up to hexanes (70%:30%). Concentration of the product containing fractions provided the above subtitle compound (0.65 g, 70%) as a cream colored solid. $^1$H NMR (300 MHz, CDCl$_3$, ppm) δ 1.46 (t, J=7 Hz, 3H), 3.98 (s, 3H), 4.13 (q, J=7 Hz, 2H), 5.44 (s, 1H), 5.68 (br s, 1H), 6.80 (d, J=8 Hz, 1H), 6.99 (dd, J=8 Hz, J$_2$=2 Hz, 1H), 7.13 (d, J=2 Hz, 1H), 7.15-7.35 (m, 4H); $^{13}$C NMR (75 MHz, CDCl$_3$, ppm) δ 15.1, 34.4, 51.2, 64.9, 111.6, 114.6, 120.0, 126.2, 127.7, 128.6, 129.4, 132.2, 135.1, 135.9, 146.0, 146.2; MS calculated for C16H16O2S2-H 303 observed 303.

Example 6

Preparation of 5-(4H-benzo[d][1,3]dithiin-2-yl)-2,3-dimethoxyphenol

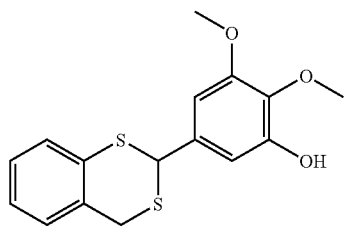

Hydrogen chloride gas was bubbled for three minutes at 22° C. through a solution of 3-hydroxy-4,5-dimethoxybenzaldehyde (0.55 g, 3.0 mmol) and 2-(mercaptomethyl)benzenethiol (0.52 g, 3.3 mmol) in dichloromethane (15 ml). After an additional 15 min., the reaction mixture was poured into saturated NaHCO$_3$ (50 ml) and extracted with dichloromethane (2×75 ml). The combined organic layer was washed with brine (30 ml), dried (Na$_2$SO$_4$), filtered and concentrated providing a crude solid. This solid was triturated with hexane and then purified by flash chromatography using a gradient of hexanes (100%) up to hexanes (70%:30%). Concentration of the product containing fractions provided the above subtitle compound (0.76 g, 78%) as a white solid. $^1$H NMR (300 MHz, CDCl$_3$, ppm) δ 3.84 (s, 3H), 3.90 (s, 3H), 3.94 (d, J=15 Hz, 1H), 4.00 (d, J=15 Hz, 1H), 5.42 (s, 1H), 5.89 (br s, 1H), 6.63 (d, J=2 Hz, 1H), 6.78 (d, J=2 Hz, 1H), 7.15-7.36 (m, 4H); $^{13}$C NMR (75 MHz, CDCl$_3$, ppm) δ 34.3, 51.5, 56.0, 61.0, 104.1, 108.2, 126.4, 127.7, 128.5, 129.6, 135.2, 135.3, 135.5, 135.7, 149.4, 152.5; MS calculated for C16H16O3S2-H 319 observed 319.

Example 7

Preparation of 4-(4H-benzo[d][1,3]dithiin-2-yl)benzonitrile

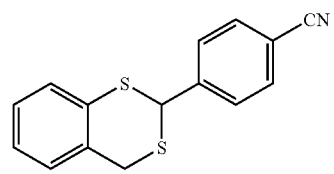

Hydrogen chloride gas was bubbled for three minutes at 22° C. through a solution of the product from step a) (0.41 g, 3.1 mmol) and 2-(mercaptomethyl)benzenethiol (0.54 g, 3.5 mmol) in dichloromethane (16 ml). After an additional 15 min., the reaction mixture was poured into saturated NaHCO$_3$ (50 ml) and extracted with dichloromethane (2×75 ml). The combined organic layer was washed with brine (30 ml), dried (Na$_2$SO$_4$), filtered and concentrated providing a crude solid. This solid was triturated with hexane and then purified by flash chromatography using a gradient of hexanes (100%) up to hexanes (70%:30%). Concentration of the product containing fractions provided the above subtitle compound (0.44 g, 52%) as a white solid. $^1$H NMR (300 MHz, CDCl$_3$, ppm) δ 3.92 (d. J=14 Hz, 1H), 3.97 (d, J=14 Hz, 1 H), 5.51 (s, 1H), 7.20-7.40 (m, 4H), 7.50-7.57 (m, 2H), 7.59-7.70 (m, 2H); $^{13}$C NMR (75 MHz, CDCl$_3$, ppm) δ 33.6, 50.4, 112.2, 118.6, 127.3, 128.1, 128.4, 129.0, 130.4, 132.6, 134.2, 136.8, 145.7: MS calculated for C15H11NS2-H 268 observed 268.

Example 8

A 0.1% w/w solution of 5-(4H-benzo[d][1,3]oxathiin-2-yl)-2-methoxyphenol was prepared in ethanol and diluted, with good mixing, into de-ionized water: thereby, generating a 1 ppm solution of 5-(4H-benzo[d][1,3]oxathiin-2-yl)-2-methoxyphenol in water. This solution was tasted using de-ionized water as the control. Comments on flavor properties relative to the control included: sweet, cooling and lingering.

Example 9

A pistachio-flavored sweetened milk was prepared using 87.52% by weight of 2% reduced fat milk, 10% by weight of granulated fruit sugar, 1.4% w/w of FD&C Blue #1 (0.01% w/w in water), 0.8% w/w of FD&C yellow #5 (0.1% w/w in water). 0.2% w/w of natural pistachio flavor (Givaudan) and 0.08% of a 0.10% w/w solution of 5-(4H-benzo[d][1,3]oxathiin-2-yl)-2-methoxyphenol in ethanol generating a 0.8 ppm sample. The control was prepared the same by increasing the milk to 87.6% and leaving out 5-(4H-benzo[d][1,3] oxathiin-2-yl)-2-methoxyphenol. Comments on flavor modification included: enhanced flavor impact, sweeter, cooling, enhanced creaminess, enhanced nutty character, sour aftertaste and brighter.

Example 10

A desired quantity of taffy was chipped off using hammer and chisel and melted in the microwave for 5-30 seconds depending on batch size. Next, 1.2% w/w of a cantaloupe flavor (Givaudan) was added to 98.26% w/w sample of the taffy followed by 0.4% w/w of granular malic acid and 0.14% w/w of 5-(4H-benzo[d][1,3]oxathiin-2-yl)-2-methoxyphenol (0.1% w/v in EtOH). The control sample was produced the same by increasing the taffy base to make up for the absence of 5-(4H-benzo[d][1,3]oxathiin-2-yl)-2-methoxyphenol in the formula. In both the control and the experimental sample, the contents were well mixed by hand while wearing gloves. The taffy was shaped into individual portions and covered in an airtight container overnight. Comments on flavor modification included: sweeter, cooling, enhanced sourness, salivating, aroma enhancement and increased impact.

Example 11

A 20 ppm solution of 5-(4H-benzo[d][1,3]oxathiin-2-yl)-2,3-dimethoxyphenol (0.1% w/w in EtOH) was prepared in de-ionized water. The resulting solution was evaluated against de-ionized water as the control. Comments on flavor properties included: cooling, sweet, burns tongue, lingering sweetness, bitter and lingering cooling.

Example 12

Granulated fruit sugar, 10% w/w, 0.25% w/W of citric acid, 0.24% w/w of FD&C yellow #5 (0.1% w/w in water), 0.24% of FD&C blue #1 (0.01% w/w in water), 0.1% w/w 15 fold lime oil (1.0% w/w in EtOH), 0.03% w/v of sodium citrate and 0.07% w/w of 5-(4H-benzo[d][1,3]oxathiin-2-yl)-2,3-dimethoxyphenol (1.0% w/w in EtOH) were added to 89.07% w/v of de-ionized water. The control was prepared by eliminating 5-(4H-benzo[d][1,3]oxathiin-2-yl)-2,3-dimethoxyphenol and increasing the water content to 89.14%. Comments on flavor modification included: sweet, cooling, astringent, juicy, mouth-watering and tart/bite.

Example 13

A 0.08% w/w sample of 5-(4H-benzo[d][1,3]oxathiin-2-yl)-2,3-dimethoxyphenol (1.0% w/w in EtOH) was added to 99.92% w/w CoolMint Listerine™ and the contents were mixed well. The resulting mixture was tasted using CoolMint Listerine™ as the control. Comments on flavor modification included: retronasal burn, cooling enhancement, intensifies flavor, increased eucalyptus, slow onset then strong burn, sweet and alcohol enhancement.

Example 14

One gram of a 1000 ppm solution of 2-(4-methoxyphenyl)-4H-benzo[d][1,3]oxathiine in EtOH was added to 99 grams of water generating a 10 ppm taste solution. This solution was tasted relative to water. Comments on flavor properties included: cooling, slightly anisic, lingering cooling.

Example 15

Five grams of sugar, 1 gram of a 1% solution of lemon flavor in EtOH and 1 gram of a 1000 ppm solution of 2-(4-methoxyphenyl)-4H-benzo[d][1,3]oxathiine in EtOH were added to 93 grams water. The resulting solution was tasted relative to a control made up of 5 g sugar, 1 gram lemon flavor and 94 g water. Comments on flavor modification included: cooling, anise, sweeter, bitter peel, more acidic, tingle, lingering flavor, better aroma and refreshing.

Example 16

One gram of a 1000 ppm solution of 4-(4H-benzo[d][1,3]oxathiin-2-yl)phenol in EtOH was added to 99 grams of water generating a 10 ppm taste solution. This solution was tasted relative to water. Comments on flavor properties included: slightly sweet and slightly alliaceous.

Example 17

Five grams of sugar, 1 gram of a 1% solution of lemon flavor in EtOH and 1 gram of a 1000 ppm solution of 4-(4H-benzo[d][1,3]oxathiin-2-yl)phenol in EtOH were added to 93 grams water. The resulting solution was tasted relative to a control made up of 5 g sugar, 1 gram lemon flavor and 94 g water. Comments on flavor modification included: cooling, dirty, sweeter, lemon peel, nutty and bitter.

Example 18

Natural almond flavor 0.01 g and 0.01 g of a 1% solution of 4-(4H-benzo[d][1,3]oxathiin-2-yl)benzonitrile in EtOH were added to 99.98 g of 2% milk and the contents were mixed well. This solution was tasted relative to the control, which was made up of 0.01 g of natural almond flavor and 99.99 g of 2% milk. Comments on flavor modification included: stronger flavor, more toasted note, earthy note, more authentic, cooling, bitter almond like, sweeter, more nutty and nut skin.

Example 19

Vanilla ice cream was thawed in the microwave for 20 seconds. Next, 0.02 g of N&A banana ice cream flavor and 0.02 g of a 1% solution of 5-(4H-benzo[d][1,3]oxathiin-2-yl)-2-ethoxyphenol in EtOH were added to 99.96 g of the thawed vanilla ice cream. The resulting mixture was mixed well with a spoon and tasted relative to the control, which was made up of 0.02 g of the N&A banana flavor in 99.98 g of the thawed vanilla ice cream. Comments on flavor modification included: enhances flavor, makes the banana riper, increases creaminess, sweeter and cooling.

It will be understood that the embodiments described herein are merely exemplary and that variations and modifications can be made by one skilled in the art without departing from the spirit and the scope of the invention. It should be understood that the embodiments described above are not only in the alternative, but can be combined.

I claim:
1. A method of providing a cooling sensation to the skin or the mucous membranes of the body, comprising the application thereto of at least one compound of Formula I

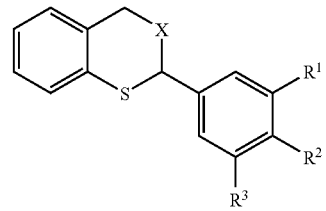

in which X is selected from S and O, $R^1$ is selected from H and OMe, $R^2$ is selected from OH, OMe and OEt, and $R^3$ is selected from H and OH.

2. A method of providing a cooling sensation to the skin or the mucous membranes of the body, comprising the application thereto of a compound selected from the group consisting of at least one of 5-(4H-benzo[d][1,3]oxathiin-2-yl)-2-ethoxyphenol; 5-(4H benzo[d][1,3]oxathiin-2-yl)-2-methoxyphenol; 4-(4H-benzo[d][1,3]oxathiin-2-yl)phenol; 4-(4H-benzo[d][1,3]oxathiin-2-yl)benzonitrile; 5-(4H benzo[d][1,3]dithiin-2-yl)-2-ethoxyphenol; 5-(4H-benzo[d][1,3]dithiin-2-yl)-2 methoxyphenol; 4-4H-benzo[d][1,3]dithiin-2-yl)phenol; 4-(4H benzo[d][1,3]dithiin-2-yl)benzonitrile; or mixtures thereof.

3. A method of providing simultaneously to the mouth cooling and sweetening effects, comprising applying to the mouth a compound selected from the group consisting of at least one of 5-(4H-benzo[d][1,3]oxathiin-2-yl)-2-ethoxyphenol; 5-(4H benzo[d][1,3]oxathiin-2-yl)-2-methoxyphenol; 4-(4H-benzo[d][1,3]oxathiin-2 yl)phenol; 5-(4H-benzo[d][1,3]dithiin-2-yl)-2-ethoxyphenol; 5-(4H-benzo[d][1,3]dithiin-2-yl)-2-methoxyphenol; 4-(4H-benzo[d][1,3]dithiin-2-yl)phenol; 4-(4H-benzo[d][1,3]dithiin-2-yl)benzonitrile; or mixtures thereof.

4. A compound selected from the group consisting of at least one of 4-(4H-benzo[d][1,3]oxathiin-2-yl)benzonitrile; 5-(4H-benzo[d][1,3]oxathiin-2-yl)-2,3-dimethoxyphenol; 4-(4H-benzo[d][1,3]dithiin-2-yl)phenol; 4-(4H-benzo[d][1,3]dithiin-2-yl)benzonitrile; 5-(4H-benzo[d][1,3]dithiin-2-yl)-2,3-dimethoxyphenol; or mixtures thereof.

5. The compound of claim 4 which is 4-(4H-benzo[d][1,3]oxathiin-2-yl)benzonitrile.

6. The compound of claim 4 which is 5-(4H-benzo[d][1,3]oxathiin-2-yl)-2,3-dimethoxyphenol.

7. The compound of claim 4 which is 4-(4-(4H-benzo[d][1,3]dithiin-2-yl)phenol.

8. The compound of claim 4 which is 4-(4H-benzo[d][1,3]dithiin-2-yl)benzonitrile.

9. The compound of claim 4 which is 5-(4H-benzo[d][1,3]dithiin-2-yl)-2,3-dimethoxyphenol.

10. A product having a cooling effect on the skin and mucous membranes of the body, comprising a compound of Formula I

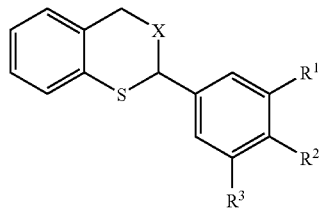

in which X is selected from S and O, $R^1$ is selected from H and OMe, $R^2$ is selected from OH, OMe and OEt, and $R^3$ is selected from H and OH.

11. A product having both cooling and sweetening effects on the mouth, comprising at least one of 5-(4H-benzo[d][1,3]oxathiin-2-yl)-2-ethoxyphenol; 5-(4H-benzo[d][1,3]oxathiin-2-yl)-2-methoxyphenol; 4-(4H-benzo[d][1,3]oxathiin-2-yl)phenol; 5-(4H-benzo[d][1,3]dithiin-2-yl)-2-ethoxyphenol; 5-(4H benzo[d][1,3]dithiin-2-yl)-2-methoxyphenol; 4-(4H-benzo[d][1,3]dithiin-2 yl)phenol; 4-(4H-benzo[d][1,3]dithiin-2-yl)benzonitrile; or mixtures thereof.

* * * * *